US00PP14279P29

(12) United States Plant Patent
Hanes

(10) Patent No.: US PP14,279 P2
(45) Date of Patent: Nov. 4, 2003

(54) PETUNIA PLANT NAMED 'JAM LAVER'

(50) Latin Name: *Petunia hybrida*
Varietal Denomination: Jam Laver

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,061
(22) Filed: Mar. 13, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by lavender colored flowers, compact habit and good basal branching.

1 Drawing Sheet

Genus and species: *Petunia hybrida.*
Variety denomination: 'Jam Laver'.

BACKGROUND OF THE NEW PLANT

The present invention comprises a new and distinct cultivar of petunia, botanically known as *Petunia hybrida,* and hereinafter referred to by the cultivar name 'Jam Laver'. The new cultivar is asexually reproduced from vegetative cuttings and tissue culture resulting from the cross of the seed/pod parent 00-385-1, a blue rose proprietary line that is unnamed and unpatented×00-423-1, a light purple proprietary line that is unnamed and unpatented.

'Jam Laver' is a product of a planned breeding program intended to create new petunia plants with lavender colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Jam Laver'. The data, which defines these characteristics, were collected from asexual reproductions carried out in Gilroy, Calif. The plant history was taken on 5 months old plants grown in one-gallon pots in fall/winter season, in a poly-covered greenhouse under 2–4 hours supplemental light and color readings were taken in the greenhouse in the winter season under natural light. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Petunia hybrida.*
*Commercial.*—Petunia.
Form: Semi upright and decumbent.
Growth and branching habit: Good vigorous habit, well-branched, full plant.
Height: From soil level to top of blooms: Approximately 10–20 cm.
Width: Approximately 25–35 cm including flowers.
Time to produce a finished flowering plant: 11 weeks.
Outdoor plant performance: Full sun; free flowering through the summer; some heat tolerance; Used as a hanging plant, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 2.0–2.5 cm.
Width: 2.5–3.2 cm.
Leaf blade shape: Ovate/Elliptic.
Leaf margin: Entire.
Apex aspect: Acute.
Base aspect: Acuminate.
Leaf color: Upper side; a little greener than RHS 137A (green); Underside; RHS 138A (green).
Texture: Glandular hairs.
Venation: Palmate.
Venation color: RHS 145A (yellow-green).
Petiole length: 0.4–1.2 cm.
Petiole width: 0.3–0.4 cm.
Petiole color: RHS 145A (yellow-green).
Petiole texture: Glandular hairs.

THE STEM

Length: 20–30 cm.
Diameter: 0.3 1 cm.

Internode length: 0.5–0.9 cm.
Color: RHS 144A/B (yellow-green).
Texture: Glandular hairs of various sizes.
Stem anthocyanin: Small, reddish, slight irregular blotches.
Peduncle color: RHS 143A (green).
Peduncle length: 1.6–1.8 cm.
Peduncle diameter: 0.2 cm.
Peduncle texture: Many glandular hairs of various sizes.

THE BUD

Shape: Oblong.
Diameter: 0.4 cm.
Length: 1.5–2.3 cm.
Color at tight bud: RHS 145B/C (yellow-green).

THE FLOWER

Blooming habit: Continuous all through the growing season. Good floriferousness.
Inflorescence type: Flowers solitary in upper leaf axis.
Young flower color: RHS N78B (purple); overlaid with RHS N78A (purple) small blotches.
Young flower floret diameter: 5.0–5.3 cm.
Mature flower color: Front side, between RHS N78B/C (purple); between RHS 195A/B (greyed-green) mid-veins. Underside, a little lighter than RHS 75A (purple) on petals; white, RHS N155D, around the mid-veins; RHS 145A (yellow-green) mid-veins.
Corolla tube colors inside: Three concentric rings of approximately 0.3 cm diameter, RHS N155D (white) at the petal flare, RHS 161C (greyed-yellow), RHS 84C (violet) at the ovary; RHS 176A (greyed-orange) mid-veins; RHS 183C (greyed-purple) secondary veining.
Corolla tube length: 1.0–2.6 cm.
Corolla outside texture: Glandular hairs of various sizes.
Floret form and number of petals: Funnel form, 5 lobed petals (single type) fused at base.
Flower (limb) diameter: 7.8–8.5 cm.
Petal apex shape: Acute.
Petal base shape: Fused.
Petal margin: Dentate.
Waviness of petals: Moderate.
Petal lobation: Strongly-moderate.
Petal texture: Papillose.
Sepals: 5, fused at the base.
Sepal color: RHS 137A (green).
Sepal length: 2.2–2.4 cm.
Sepal width: 0.6–0.8 cm.
Sepal shape: Oblong.
Sepal apex: Acute.
Sepal texture: Glandular hairs of various sizes.
Lastingness of individual blooms: 5–8 days.
Fragrance: None.

THE REPRODUCTIVE ORGANS

Stamens: 5; 2 taller, 2 short, 1 much shorter.
Filament color: RHS 155C (white).
Pollen color: RHS 11C (yellow).
Pistil: One.
Stigma: RHS 145B (yellow-green); RHS 144A (yellow-green) center spot.
Style color: RHS 144D (yellow-green).
Fruit seed set: Not observed.

DISEASE AND INSECT RESISTANCE

Not observed.

COMPARISON WITH KNOWN CULTIVARS

Compared to its female parent 00-385-1 in the following ways: The female parent is an up right growing plant with a blue rose flower color that is late to flower while the hybrid is flatter growing, lavender flower, and early to flower.

Compared to its male parent 00-423-1 in the following ways: The male parent is a light purple free flowering plant while the hybrid is a lavender free flowering plant.

I claim:

1. A new and distinct petunia plant as shown and described herein.

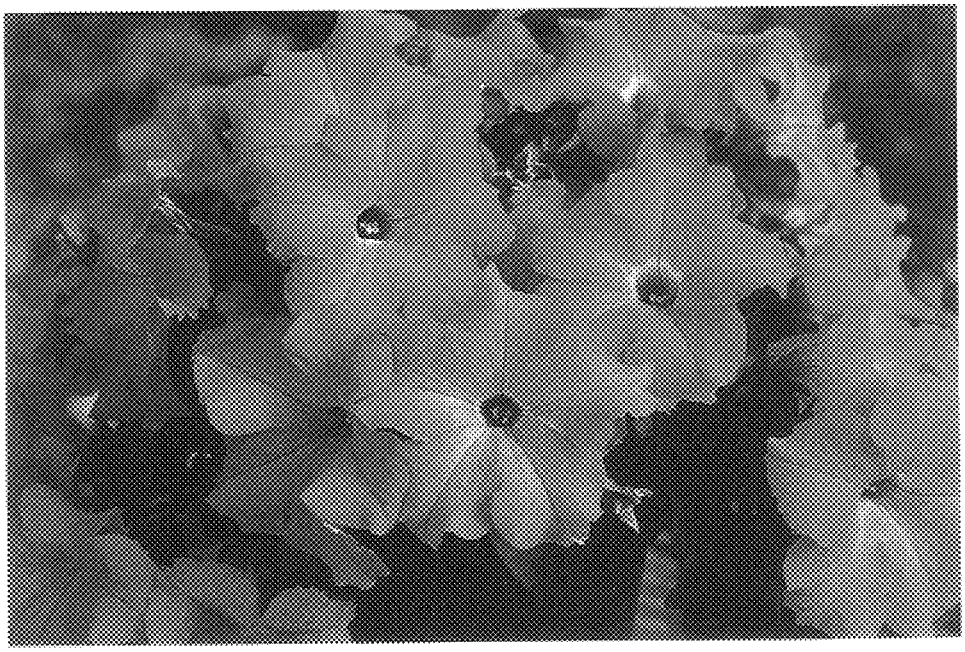

* * * * *